United States Patent [19]

Light et al.

[11] 4,126,641

[45] Nov. 21, 1978

[54] PROCESS FOR PREPARING 2-BUTYL-3,5,5-TRIMETHYL-2-CYCLOHEXEN-1,4-DIONE

[75] Inventors: Kenneth K. Light, Long Branch; Bette M. Spencer, Ocean Grove; Joaquin F. Vinals, Red Bank, all of N.J.; Jacob Kiwala; Edward J. Shuster, both of Brooklyn, N.Y.

[73] Assignee: International Flavors & Fragrances Inc., New York, N.Y.

[21] Appl. No.: 774,057

[22] Filed: Mar. 3, 1977

[51] Int. Cl.² .............................................. C07C 45/00
[52] U.S. Cl. .............................. 260/586 C; 131/17 R; 131/17 A; 252/132; 252/522; 252/545; 260/586 R; 260/340.9 R; 424/69
[58] Field of Search ....................... 260/586 R, 586 C

[56] References Cited

U.S. PATENT DOCUMENTS 3,984,475  10/1976  Tamai et al. .................... 260/586 R

OTHER PUBLICATIONS

Schulte-Elte, "Chem. Ab.", 81:91136k (1974).
Rhode, "Chem. Ab.", 79:15994g (1973).
Chapman et al., "Chem. Ab.", 75:13537d (1971).
Hegidus et al., "J.A.C.S.", 98:13, 3901-3909 (1976).

*Primary Examiner*—Norman Morgenstern
*Attorney, Agent, or Firm*—Arthur L. Liberman; Franklin D. Wolffe; Harold Haidt

[57] ABSTRACT

Processes and compositions are described for the use in tobacco, perfume and perfumed article aroma augmenting, enhancing and imparting compositions and as tobacco, perfume and perfumed article aroma augmenting, enhancing or imparting materials of 2-butyl-3,5,5-trimethyl-2-cyclohexen-1,4-dione having the formula:

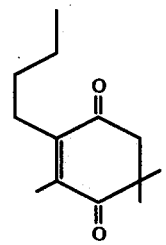

produced by reacting a ketal of 3,5,5-trimethyl-2-cyclohexen-1,4-dione such as 2,7,9,9-tetramethyl-1,4-dioxaspiro[4,5]dec-6-en-8-one with n-butyltriphenylphosphorane and then deketalizing the resulting product to form the 2-butyl-3,5,5-trimethyl-2-cyclohexen-1,4-dione. Addition of 2-butyl-3,5,5-trimethyl-2-cyclohexen-1,4-dione to consumable materials is indicated to produce:

(A) In perfumes, colognes and perfumed articles, deep, slightly woody, herbaceous aromas; and (B) In tobaccos and tobacco flavors, pungent, sweet, hay-, tea-, tobacco-like, floral and fruity notes, both prior to and on smoking in both the main stream and the side stream.

2 Claims, 1 Drawing Figure

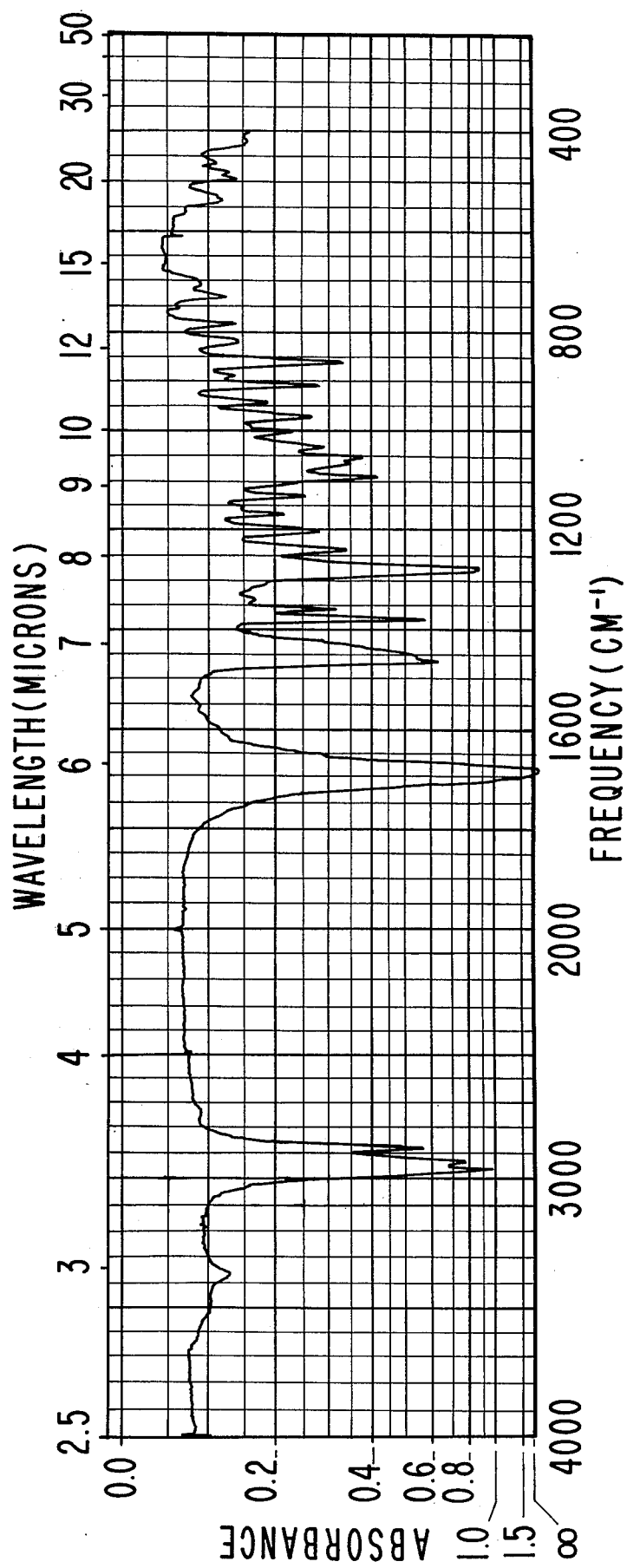

PROCESS FOR PREPARING 2-BUTYL-3,5,5-TRIMETHYL-2-CYCLOHEXEN-1,4-DIONE

BACKGROUND OF THE INVENTION

The present invention relates to 2-butyl-3,5,5-trimethyl-2-cyclohexen-1,4-dione having the formula:

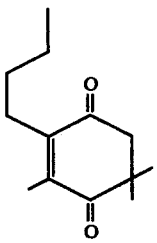

produced by the process of our invention, and novel compositions using 2-butyl-3,5,5-trimethyl-2-cyclohexen-1,4-dione to augment or enhance the flavor and/or aroma of consumable materials, or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Deep, slightly woody, herbaceous aromas are desirable in several types of perfume compositions, perfumed articles and colognes.

Pungent, sweet, hay-, tea-, tobacco-like, floral and fruity notes prior to and on smoking, in both the main stream and the side stream, are desirable in tobaccos and tobacco flavors.

U.S. Pat. No. 3,923,898 discloses the use in tobaccos and tobacco flavors of compounds having the generic structure:

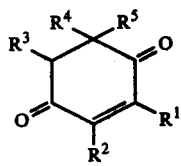

wherein one of the symbols $R^1$, $R^2$, and $R^3$ represents a lower alkyl radical, and each of the other two symbols represents a hydrogen atom; or two of the symbols $R^1$, $R^2$, and $R^3$ represent each a lower alkyl radical, and the other a hydrogen atom; and wherein each of the symbols $R^4$ and $R^5$ represent a lower alkyl radical. The specific compounds disclosed in U.S. Pat. No. 3,923,898 are 2,2,5-trimethyl-cyclohex-5-en-1,4-dione and 2,2,5,6-tetramethylcyclohex-5-en-1,4-dione. The compound of our invention, 2-butyl-3,5,5-trimethyl-2-cyclohexen-1,4-dione, however, has properties which are unexpected, unobvious, and advantageous as compared to the compounds as specified in U.S. Pat. No. 3,923,898. In addition, although the genus of 3,923,898 covers 2-butyl-3,5,5-trimethyl-2-cyclohexen-1,4-dione, 2-butyl-3,5,5-trimethyl-2-cyclohexen-1,4-dione is neither suggested nor implied therein. In addition, Danish Pat. No. 85,397 of Apr. 21, 1958, discloses a compound having the structure:

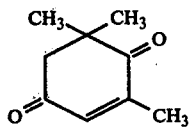

The compound, 2-butyl-3,5,5-trimethyl-2-cyclohexen-1,4-dione, of the instant invention, has properties unobvious, unexpected, and advantageous over the properties of the compound disclosed in Danish Pat. No. 85,397.

BRIEF DESCRIPTION OF THE DRAWING

FIG. 1 represents the infrared spectrum for the compound 2-butyl-3,5,5-trimethyl-2-cyclohexen-1,4-dione produced according to the process of Example II.

THE INVENTION

It has now been discovered that novel perfume compositions, colognes, and perfumed articles having deep, slightly woody, herbaceous aromas; and novel tobacco and tobacco flavor compositions having pungent, sweet, hay-, tea-, tobacco-like, floral and fruity notes, both prior to and on smoking in both the main stream and the side stream, may be provided by the utilization of 2-butyl-3,5,5-trimethyl-2-cyclohexen-1,4-dione having the structure:

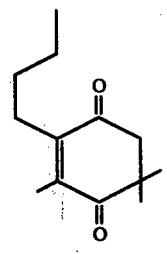

in perfumes, colognes, perfumed articles, tobaccos, and tobacco flavors.

2-Butyl-3,5,5-trimethyl-2-cyclohexen-1,4-dione useful as indicated herein may be produced according to the process of reacting n-butyltriphenylphosphorane with a ketal of 3,5,5-trimethyl-2-cyclohexen-1,4-dione such as 2,7,9,9-tetramethyl-1,4-dioxaspiro[4,5]dec-6-en-8-one. The reaction sequence including preparation of the ketal reactant (e.g., 2,7,9,9-tetramethyl-1,4-dioxaspiro[4,5]dec-6-en-8-one) is set forth as follows:

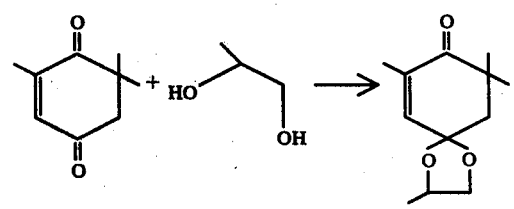

Other diols can be used to form ketals of our process, for example, ethylene glycol; 1,2-hexanediol; and 2,3-butanediol.

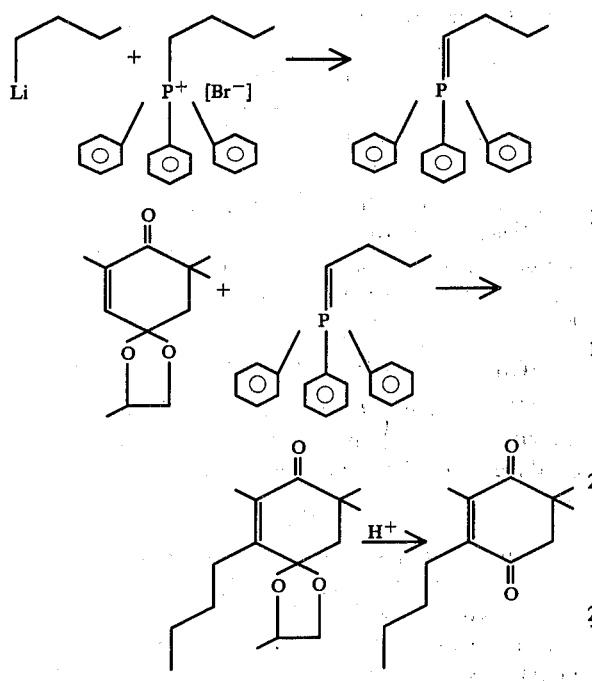

It is preferable to prepare the n-butyltriphenylphosphorane in situ in the reaction vessel where the reaction of the phosphorane with the ketal reactant (e.g., 2,7,9,9-tetramethyl-1,4-dioxaspiro[4,5]dec-6-en-8-one) is to take place. This reagent is prepared by reacting equimolar quantities of n-butyltriphenylphosphonium bromide and n-butyl lithium in the presence of an inert solvent such as benzene and/or hexane. The reaction between the triphenylphosphorane and ketal (e.g., 2,7,9,9-tetramethyl-1,4-dioxaspiro[4,5]dec-6-en-8-one) preferably takes place at room temperature, with the n-butyltriphenylphosphorane being in excess to an extent of about 50%, 3 moles triphenylphosphorane:2 moles ketal (e.g., 2,7,9,9-tetramethyl-1,4-dioxaspiro[4,5]dec-6-en-8-one). At the end of the reaction (which is exothermic), the inorganic salts produced are removed by washing with water, and the reaction product, which is a ketal, is then deketalized with mineral acid, for example, hydrochloric acid (1%), sulfuric acid, or phosphoric acid, in dilute aqueous media. The resulting product is then distilled under vacuum, preferably using a fractional distillation column or spinning band column.

The 2-butyl-3,5,5-trimethyl-2-cyclohexen-1,4-dione of our invention and one or more auxiliary perfume ingredients, including, for example, alcohols, aldehydes, nitriles, esters, cyclic esters and natural essential oils, may be admixed so that the combined odors of the individual components produce a pleasant and desired fragrance, particularly and preferably basil fragrances. Such perfume compositions usually contain (a) the main note or the "bouquet" or the foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, it is the individual components which contribute their particular olfactory characteristics; however, the overall sensory effect of the perfume composition will be at least the sum total of the effects of each of the ingredients. Thus, the 2-butyl-3,5,5-trimethyl-2-cyclohexen-1,4-dione can be used to alter, modify or enhance the aroma characteristics of a perfume composition, for example, by utilizing or moderating the olfactory reaction contributed by another ingredient in the composition.

The amount of 2-butyl-3,5,5-trimethyl-2-cyclohexen-1,4-dione of our invention which will be effective in perfume compositions as well as in perfumed articles and colognes depends on many factors, including the other ingredients, their amounts and the effects which are desired. It has been found that perfume compositions containing as little as 0.01% of 2-butyl-3,5,5-trimethyl-2-cyclohexen-1,4-dione or even less (e.g., 0.005%) can be used to impart deep, slightly woody, herbaceous aromas to soaps, cosmetics, or other products. The amount employed can range up to 70% of the fragrance components and will depend on considerations of cost, nature of the end product, the effect desired on the finished product and the particular fragrance sought.

The 2-butyl-3,5,5-trimethyl-2-cyclohexen-1,4-dione of our invention is useful [taken alone or together with other ingredients in perfume compositions] as an olfactory component in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s), as little as 1% of 2-butyl-3,5,5-trimethyl-2-cyclohexen-1,4-dione will suffice to impart an intense floral note to basil formulations. Generally, no more than 3% of 2-butyl-3,5,5-trimethyl-2-cyclohexen-1,4-dione based on the ultimate end product, is required in the perfume composition.

In addition, the perfume composition or fragrance composition of our invention can contain a vehicle or carrier for the 2-butyl-3,5,5-trimethyl-2-cyclohexen-1,4-dione. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

An additional aspect of our invention provides an organoleptically improved smoking tobacco product and additives therefor including methods of making the same which overcome problems heretofore encountered in the creation or enhancement of specific desired pungent, sweet, hay-, tea-, tobacco-like, floral and fruity notes. These notes, both prior to and on smoking in both the main stream and the side stream, may now be readily controlled and maintained at the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby desirable pungent, sweet, hay-, tea-, tobacco-like, floral and fruity notes prior to and on smoking in both the main stream and the side stream, may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing, as an active ingredient, the 2-butyl-3,5,5-trimethyl-2-cyclohexen-1,4-dione of our invention.

In addition to the 2-butyl-3,5,5-trimethyl-2-cyclohexen-1,4-dione of our invention, other flavoring and aroma additives may be added to the smoking tobacco material or substitute therefor either separately or in mixture with one or more of the cyclohexadiene derivatives:

I. Synthetic Materials

Beta-methyl-cinnamaldehyde;
Eugenol;
Dipentene;
Damascenone;
Maltol;
Ethyl maltol;
Delta undecalactone;
Delta decalactone;
Benzaldehyde;
Amyl acetate;
  Ethyl butyrate;
  Ethyl valerate;
  Ethyl acetate;
  2-Hexen-1-ol;
  2-Methyl-5-isopropyl-1,3-nonadiene-8-one;
  2-Methyl-5-isopropylacetophenone;
  2-Hydroxy-2,5,5-8a-tetramethyl-1-(2-hydroxyethyl)-decahydronaphthalene;
  Dodecahydro-3a-6,6,9a-tetramethyl naphtho(2,1-b)-furan;
  4-Hydroxyhexanoic acid, gamma lactone;
  Polyisoprenoid hydrocarbons defined in Example V of U.S. Pat. No. 3,589,372 issued on June 29, 1971.

II. Natural Oils

Celery seed oil;
Coffee extract;
Bergamot oil;
Cocoa extract;
Nutmeg oil;
Origanum oil.

An aroma and flavoring concentrate containing the 2-butyl-3,5,5-trimethyl-2-cyclohexen-1,4-dione of our invention and, if desired, one or more of the above-indicated additional flavoring additives, may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of pungent, sweet, hay-, tea-, tobacco-like, floral and fruity notes prior to and on smoking, in both the main stream and the side stream, we have found that satisfactory results are obtained if the proportion by weight of the sum total of 2-butyl-3,5,5-trimethyl-2-cyclohexen-1,4-dione and other active ingredients to smoking tobacco material is between 50 ppm and 1500 ppm (0.005%–0.15%). We have further found that satisfactory results are obtained if the proportions by weight of the sum total of 2-butyl-3,5,5-trimethyl-2-cyclohexen-1,4-dione used to flavoring material is between 0.05:1 and 0.50:1.

Any convenient method for incorporating the 2-butyl-3,5,5-trimethyl-2-cyclohexen-1,4-dione in the tobacco product may be employed. Thus the 2-butyl-3,5,5-trimethyl-2-cyclohexen-1,4-dione taken alone or along with other flavoring additives may be dissolved in a suitable solvent such as ethanol, pentane, diethyl ether and/or other volatile organic solvents, and the resulting solution may either be sprayed on the cured, cased and blended tobacco material, or the tobacco material or filter may be dipped into such solution. Under certain circumstances a solution of 2-butyl-3,5,5-trimethyl-2-cyclohexen-1,4-dione taken alone or taken further together with other flavoring additives as set forth above, may be applied by means of a suitable applicator, such as a brush or roller, on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases the tobacco treated may have the 2-butyl-3,5,5-trimethyl-2-cyclohexen-1,4-dione of our invention in excess of the amounts or concentrations above indicated so that when blended with other tobaccos, the final product will have the percentage within the desired range.

In accordance with one specific example of our invention, an aged, cured and shredded domestic burley tobacco is sprayed with a 20% ethyl alcohol solution of 2-butyl-3,5,5-trimethyl-2-cyclohexen-1,4-dione in an amount to provide a tobacco composition containing 600 ppm by weight of 2-butyl-3,5,5-trimethyl-2-cyclohexen-1,4-dione on a dry basis. Thereafter the alcohol is removed by evaporation, and the tobacco is manufactured into cigarettes by the usual techniques. The cigarette, when treated as indicated, has desirable and pleasant pungent, sweet, hay-, tea-, tobacco-like, floral and fruity notes which are detectable in the main stream and the side streams when the cigarette is smoked.

While our invention is particularly useful in the manufacture of smoking tobacco such as cigarette tobacco, cigar tobacco and pipe tobacco, other tobacco products formed from sheeted tobacco dust or fines may also be used. As stated supra, the 2-butyl-3,5,5-trimethyl-2-cyclohexen-1,4-dione of our invention can be incorporated with materials such as filter tip materials, seam paste, packaging materials, and the like, which are used along with the tobacco to form a product adapted for smoking. Furthermore, the 2-butyl-3,5,5-trimethyl-2-cyclohexen-1,4-dione of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

It will thus be apparent that the 2-butyl-3,5,5-trimethyl-2-cyclohexen-1,4-dione of our invention can be utilized to alter, modify, or enhance sensory properties, particularly organoleptic properties, such as flavor(s) and/or fragrance(s) of a wide variety of consumable materials.

The following examples serve to illustrate our invention, and this invention is considered restricted thereto only as indicated in the appended claims.

All parts and percentages given herein are by weight unless otherwise specified.

EXAMPLE I

PREPARATION OF 2,7,9,9-TETRAMETHYL-1,4-DIOXASPIRO[4,5]-DEC-6-EN-8-ONE

Reaction:

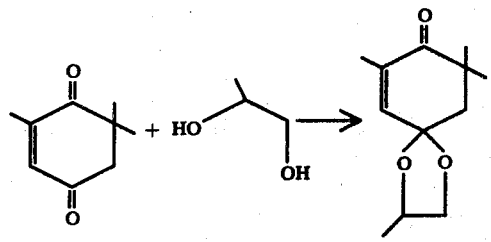

To a 2-liter flask fitted with a reflux condenser, a water separator, and a stirrer is charged 265 g of 2,6,6-trimethylcyclohex-2-en-1,4-dione (prepared by the method described in Helv. Chim. Acta 39, 2041 [1956]), 2669 g of propylene glycol, 500 ml of benzene, and 1 g of p-toluene-sulfonic acid. The reactants are stirred and refluxed until no additional water is collected in the water separator. The product is washed with water to a pH of 6, and the solvent is stripped off. The residue is vacuum distilled through a 9" Goodloe column to yield 257 g of product, boiling point 92° at 1 mm Hg (80% yield).

EXAMPLE II

PREPARATION OF 2-BUTYL-3,5,5-TRIMETHYL-2-CYCLOHEXEN-1,4-DIONE

Reaction:

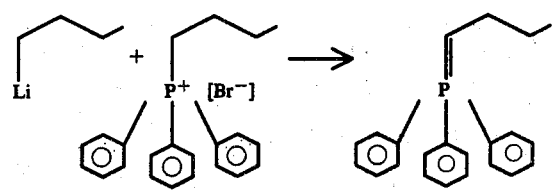

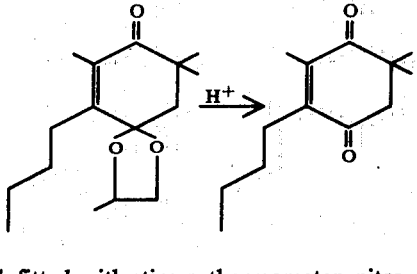

A 1 liter flask fitted with stirrer, thermometer, nitrogen inlet tube, reflux condenser and dropping funnel is charged with 120 g (0.3 moles) of n-butyltriphenylphosphonium bromide and 500 ml benzene. A solution of 2.3 molar n-butyl lithium in hexane (126 ml, 0.29 moles) is added dropwise over 30 minutes. The temperature rises from 20° C. to 42° C., and the solution turns dark red. The mixture is stirred for 1 hour at ambient temperature, followed by the addition of 42 g (0.2 moles) of 2,7,9,9-tetramethyl-1,4-dioxaspiro[4,5]dec-6-en-8-one (prepared by the method of Example I) over a 20-minute period. A slight exotherm is noted, and the color of the solution changes from red to brown. After stirring for an additional 6 hours at ambient temperature, the inorganic salts are removed by washing with water. The product is then stirred at room temperature with 200 ml of 1% hydrochloric acid to deketalize the product. The progress of the deketalization is monitored by GLC (10' × ⅛" SE 30 column, programmed from 80° to 220° C. at 8°/min). When no further change is noted (36 hours at room temperature), the organic layer is separated, and the solvent is stripped off. The residue is distilled, and 29.4 g of material (boiling point 80°–108° C. at 0.6 mm Hg) is obtained. This material is redistilled on a spinning band column yielding 18 g of 2-butyl-3,5,5-trimethyl-2-cyclohexen-1,4-dione (boiling point 88° C. at 0.5 mm Hg) with a purity of greater than 90% (39% yield). The compound exhibited the following spectral characteristics.

| NMR (δ) ppm | |
|---|---|
| ppm | Interpretation |
| 2.48 (2H) | AB Quartet |
| 1.80 (3H) | singlet |
| 1.50 (6H) | multiplet |
| 1.20 (3H) | singlet |
| 1.12 (3H) | singlet |
| 0.99 (3H) | triplet |

Infrared Analysis: 1670 cm$^{-1}$ (C=O).

Mass Spectral Analysis (m/e): 95, 109, 41, 96, 67, 208(m).

The IR spectrum is set forth in FIG. 1.

EXAMPLE III

The following mixture is prepared:

| Ingredients | Parts by Weight |
|---|---|
| Methyl chavicol | 40.0 |
| Linalool synthetic | 60.0 |
| Bisabolene | 2.0 |
| Nerolidol | 1.0 |
| Eugenol | 2.0 |
| Gamma terpinene | 1.0 |
| 2-Butyl-3,5,5-trimethyl-2-cyclohexen-1,4-dione | 20.0 |

The 2-butyl-3,5,5-trimethyl-2-cyclohexen-1,4-dione imparts the deep, slightly woody, herbaceous tone so necessary for the basil character of this basil formulation.

EXAMPLE IV

PREPARATION OF A COSMETIC POWDER COMPOSITION

A cosmetic powder is prepared by mixing in a ball mill 100 g of talcum powder with 0.25 g of 2-butyl-3,5,5-trimethyl-2-cyclohexen-1,4-dione prepared according to Example II. It has a deep, slightly woody, herbaceous aroma.

EXAMPLE V

PERFUMED LIQUID DETERGENT

Concentrated liquid detergents (Lysine salt of n-dodecylbenzene sulfonic acid as more specifically described in U.S. Pat. No. 3,948,818, issued on Apr. 6, 1976) with a deep, slightly woody, herbaceous aroma, are prepared containing 0.10%, 0.15%, and 0.20% of 2-butyl-3,5,5-trimethyl-2-cyclohexen-1,4-dione prepared according to Example II. They are prepared by adding and homogeneously mixing the appropriate quantity of 2-butyl-3,5,5-trimethyl-2-cyclohexen-1,4-dione in the liquid detergent. The detergents all possess a deep, slightly woody, herbaceous aroma, the intensity increasing with utilization of greater concentrations of 2-butyl-3,5,5-trimethyl-2-cyclohexen-1,4-dione.

EXAMPLE VI

PREPARATION OF A COLOGNE AND HANDKERCHIEF PERFUME

2-Butyl-3,5,5-trimethyl-2-cyclohexen-1,4-dione prepared according to the process of Example II is incorporated in a cologne at a concentration of 2.5% in 85% aqueous ethanol; and into a handkerchief perfume at a concentration of 20% (in 95% aqueous ethanol). A distinct and definite deep, slightly woody, herbaceous aroma is imparted to the cologne and to the handkerchief perfume.

EXAMPLE VII

PREPARATION OF SOAP COMPOSITION

One hundred grams of soap chips are mixed with 1 gram of 2-butyl-3,5,5-trimethyl-2-cyclohexen-1,4-dione of Example II until a homogeneous composition is obtained. The perfumed soap composition manifests a deep, slightly woody, herbaceous aroma.

EXAMPLE VIII

PREPARATION OF A DETERGENT COMPOSITION

A total of 100 g of a detergent powder (Lysine salt of n-dodecylbenzene sulfonic acid as more specifically described in U.S. Pat. No. 3,948,818, issued on Apr. 6, 1976) is mixed with 0.15 g of 2-butyl-3,5,5-trimethyl-2-cyclohexen-1,4-dione of Example II until a substantially homogeneous composition is obtained. This composition has a deep, slightly woody, herbaceous aroma.

EXAMPLE IX

PREPARATION OF A COLOGNE AND HANDKERCHIEF PERFUME

The composition of Example III is incorporated in a cologne at a concentration of 2.5% in 85% aqueous ethanol; and into a handkerchief perfume at a concentration of 20% (in 95% aqueous ethanol). The use of 2-butyl-3,5,5-trimethyl-2-cyclohexen-1,4-dione in the composition of Example III affords a distinct basil character having deep, slightly woody and herbaceous notes.

EXAMPLE X

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes, and the following formulation is compounded and incorporated into each of these cigarettes.

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with 2-butyl-3,5,5-trimethyl-2-cyclohexen-1,4-dione produced according to Example II, at 100 ppm per cigarette. Another one-third of these model cigarettes are treated in the filter with 2-butyl-3,5,5-trimethyl-2-cyclohexen-1,4-dione produced according to Example II at the rate of $2 \times 10^{-5}$ and $3 \times 10^{-5}$ gm. When evaluated by paired comparison, the cigarettes treated both in the tobacco and in the filter with the 2-butyl-3,5,5-trimethyl-2-cyclohexen-1,4-dione are found, in smoke flavor, to be more tobacco-like with enhanced Virginia tobacco-like notes.

What is claimed is:

1. The process for preparing 2-butyl-3,5,5-trimethyl-2-cyclohexen-1,4-dione having the structure:

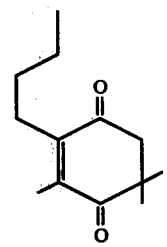

comprising the steps of:
(I) Forming a mono-ketal of 3,5,5-trimethyl-2-cyclohexen-1,4-dione, whereby the ketal moiety is at the "1" position;
(II) Mixing said ketal with n-butyltriphenylphosphorane thereby forming a ketal of 2-butyl-3,5,5- trimethyl-2-cyclohexen-1,4-dione, the ketal moiety being at the "1" position;
(III) Hydrolyzing said ketal of 2-butyl-3,5,5-trimethyl-2-cyclohexen-1,4-dione to said dione, the hydrolysis taking place in acid media.

2. The process of claim 1 wherein the mono-ketal of 3,5,5-trimethyl-2-cyclohexen-1,4-dione is formed by reaction of 1,2-propanediol with 3,5,5-trimethyl-2-cyclohexen-1,4-dione.

* * * * *